US00PP12396P2

(12) United States Plant Patent
Heims

(10) Patent No.: US PP12,396 P2
(45) Date of Patent: Feb. 5, 2002

(54) TIARELLA PLANT NAMED 'IRON BUTTERFLY'

(75) Inventor: Dan M. Heims, Portland, OR (US)

(73) Assignee: Terra Nova Nurseries, Inc., Tigard, OR (US)

( * ) Notice: Subject to any disclaimer, the term of this patent is extended or adjusted under 35 U.S.C. 154(b) by 0 days.

(21) Appl. No.: 09/324,627

(22) Filed: Jun. 2, 1999

(51) Int. Cl.[7] ..... A01H 5/00
(52) U.S. Cl. ..... Plt./263
(58) Field of Search ..... Plt./263

*Primary Examiner*—Bruce R. Campell
*Assistant Examiner*—Anne Marie Grunberg
(74) *Attorney, Agent, or Firm*—Klarquist Sparkman, LLP

(57) ABSTRACT

A new and distinct hybrid of Tiarella plant characterized by unique leaves.

1 Drawing Sheet

The present invention relates to a new and distinct hybrid of Tiarella which originated as a cross-pollination of 2 unnamed seedlings; Tiarella Seedling 97-8 (unpatented) (seed parent), a very well-marked plant of moderate vigor and small cream-colored flowers, and Tiarella Seedling 97-63 (unpatented) (pollen parent), an extremely vigorous plant with large, pink tinted flowers, and moderate markings, in the Saxifrage family (Saxifragaceae). Neither parent is named or patented. Due to the fact that the parents are from interspecific crosses and several species are involved, no species designations can be given.

The new variety has been reproduced only by asexual propagation (division and tissue culture). Each of the progeny exhibits identical characteristics to the original plant and is unlike any Tiarella offered by any American nursery or book, known to the inventor, as evidenced by the following characteristics:

Unique form and foliage shape and color.

Asexual propagation by division and tissue-culture as done in Canby, Oreg., shows that the foregoing characteristics and distinctions come true to form and are established and transmitted through succeeding propagations.

BRIEF DESCRIPTION OF THE PHOTOGRAPH

The FIGURE is an example of foliage and flowers.

DETAILED PLANT DESCRIPTION

The following is a detailed description of the new Tiarella hybrid based on observations of two year old specimens grown in a cool greenhouse in Canby, Oreg. The color descriptions are all based on The Royal Horticultural Society Colour Chart.

Plant:

*Form and hardiness.*—Herbaceous perennial; retains foliage in USDA hardiness Zones 6 to 9, dies back in USDA hardiness zones 4 and 5.

*Habit.*—Clumping.

*Size.*—To 60 cm wide and 35 cm high.

Leaf:

*Type.*—Simple.

*Arrangement.*—Rosette.

*Shape.*—Palmate, deeply 7-lobed, irregularly toothed; central lobe elongated, tapers to a fine point from a narrow base; lobe tip finely incised. Lobes #3 and #5 ovelap lobe #4 slightly; central lobe emerges from the petiole beneath the other lobes.

*Length.*—8–10 cm.

*Width.*—8–10 cm.

*Petiole length.*—12–15 cm.

*Margins.*—Crenate, each tooth abruptly pointed.

*Apex.*—Acuminate with the very tip mucronulate.

*Base.*—Cordate.

*Texture.*—Slightly rugose, velvet-matte finish. Upper surface hairs 0.2–0.3 cm. apart, and no hairs on lower surface.

*Venation.*—Palmate-reticulate.

Flower:

*Fragrant.*—Yes.

*Petal count.*—5 petals, 5 calyx lobes.

*Petal shape.*—Triangular, clawed.

*Flower type.*—Complete, calyx tube campanulate, ovary superior.

*Flower size.*—To 1 cm wide from petal tip to petal tip.

*Flower number.*—40–55 blooms per raceme.

*Blooming habit.*—Simple upright raceme to 30 cm. high and 1.5 cm wide with 30–35 racemes at one time per second-year plant.

*Bloom period.*—Early April to June. Minor sporadic rebloom in summer and fall.

Fruit:

*Type.*—A one-celled, horned capsule.

*Fertile.*—Yes.

Disease tolerance: Excellent disease resistance to powdery mildew, a common problem of Tiarella.

Color characteristics:

*Foilage.*—Upper surface: RHS Green Group 137B marked with RHS Black Group 202A along each lobe's central vein, major lateral veins, and the leaf center. Lower surface: RHS 191 A–B Greyed-Green Group.

*Peduncle.*—Yellow Green 146C to an overlay of Red Purple 70C.

*Flower bud.*—RHS Red Purple Group 65B.

*Flowers.*—Sepal and petal color inside and stamens, RHS Purple Group 75D; sepals outside, RHS Purple Group 75C; pollen color, RHS Yellow orange Group 17A.

Growth in season: A plant from a 72-plug tray measuring 6 cm wide in diameter can spread to 30–35 cm wide in diameter in one season of growth under good growing conditions.

DESCRIPTION OF PARENT PLANTS

This Tiarella's parents: Seedling 97-8 (unpatented) (seed parent), a very well marked plant of moderate vigor and small cream-colored flowers, an Seedling 97-63 (unpatented) (pollen parent), and extremely vigorous plant with large, pink tinted flowers, and moderate markings, in the Saxifrage family (Saxifragaceae). This Tiarella hybrid (Tiarella 'Iron Butterfly') has characteristics that make it unique from its parents: intense dark markings on upper surface, deeply cut leaves, extreme vigor, and large light pink flowers.

I claim:

1. A new and distinct hybrid of Tiarella plant substantially as shown and described, characterized by unique leaf color and form.

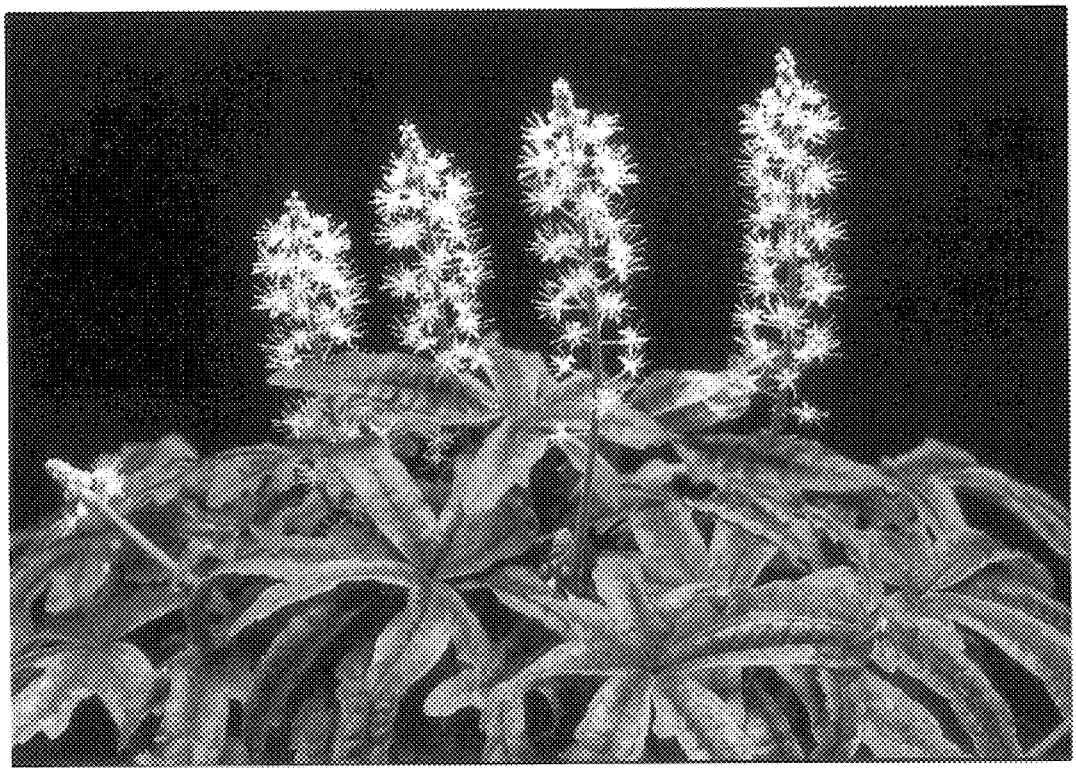

* * * * *